United States Patent
Schoeckert et al.

[11] Patent Number: 5,546,950
[45] Date of Patent: Aug. 20, 1996

[54] ELECTROCARDIOGRAPIC PATIENT LEAD CABLE APPARATUS

[75] Inventors: Kurt P. Schoeckert, New Berlin; David W. Mortara, River Hills, both of Wis.

[73] Assignee: Mortara Instrument, Inc., Milwaukee, Wis.

[21] Appl. No.: 271,051

[22] Filed: Jul. 6, 1994

[51] Int. Cl.⁶ ................................................. A61B 5/0402
[52] U.S. Cl. .......................... 128/696; 128/639; 439/502; 439/623; 439/909
[58] Field of Search ...................... 128/639–641, 128/644, 696; 439/498, 502, 623, 909

[56] References Cited

U.S. PATENT DOCUMENTS

| | | | |
|---|---|---|---|
| 4,082,086 | 4/1978 | Page et al. | 128/640 |
| 4,328,814 | 5/1982 | Arkans | 128/640 |
| 4,353,372 | 10/1982 | Ayer | 128/640 |
| 4,425,921 | 1/1984 | Fujisaki | 128/644 |
| 4,957,109 | 9/1990 | Groeger | 128/640 |
| 5,203,720 | 4/1993 | Zini | 439/502 |
| 5,265,579 | 11/1993 | Ferrari | 128/640 |
| 5,341,812 | 8/1994 | Allaire et al. | 128/696 |
| 5,370,116 | 12/1994 | Rollman et al. | 128/644 |

FOREIGN PATENT DOCUMENTS 2185403  7/1987  United Kingdom.

Primary Examiner—Lee S. Cohen
Attorney, Agent, or Firm—Andrus, Sceales, Starke & Sawall

[57] ABSTRACT

An electrocardiographic patient lead cable apparatus comprises an elongated cable part and a connector. The cable part has a plurality of connecting wires with connectors for the electrodes. The connecting wires are joined together for varying portions of their length to form a flat common portion of the cable part. The common portion is connected at one end to the connector. The connecting wires separate from the common portion at the selected locations along the extension of the common part from the end connected to the connector to form relatively short separated connecting wires. The lead cable apparatus so formed facilitates correct connection of electrodes positioned at various locations on the body of the patient and reduces or eliminates tangling of the connecting wires. The connector is of compact, lightweight construction.

21 Claims, 1 Drawing Sheet

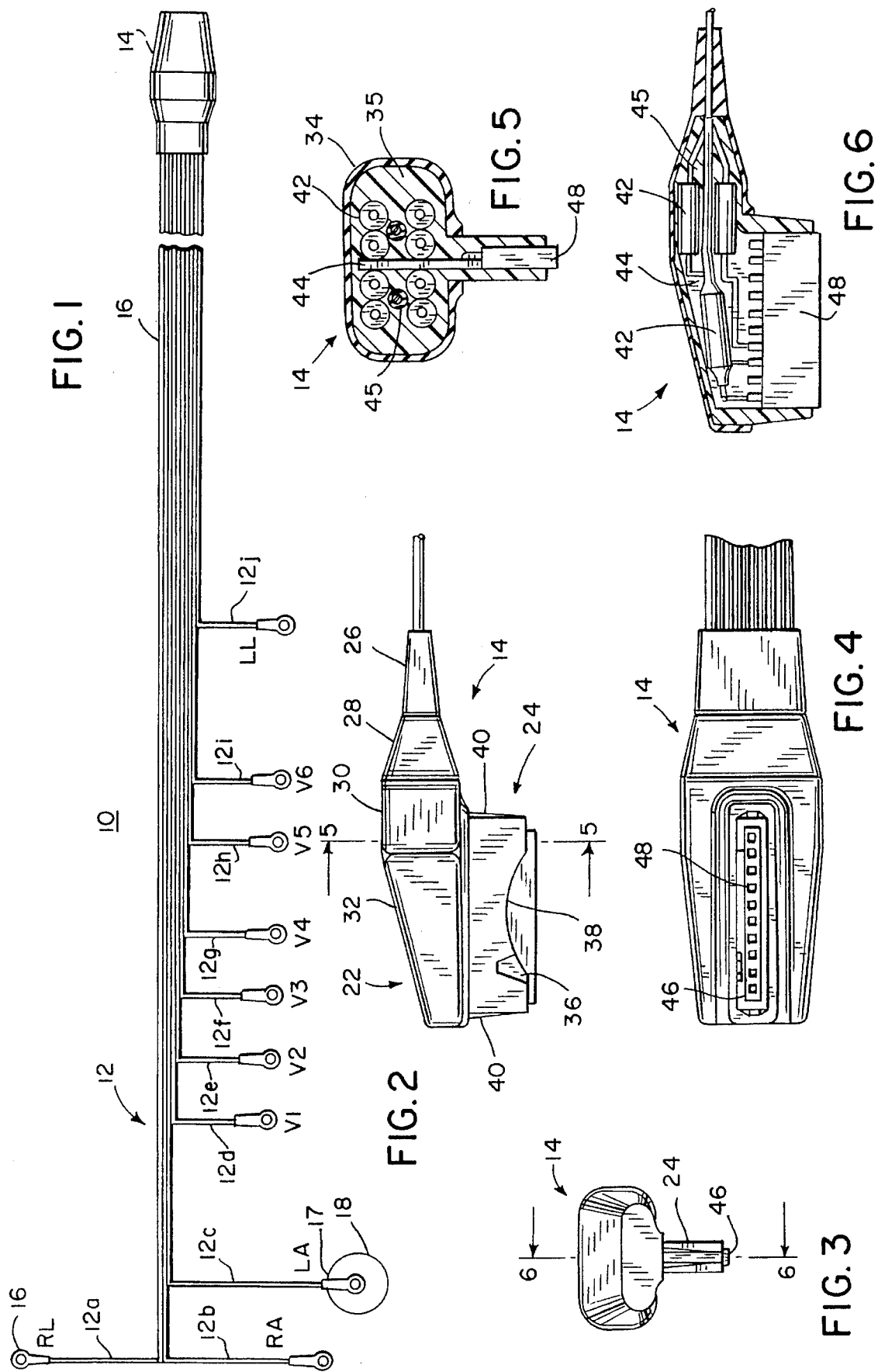

ELECTROCARDIOGRAPIC PATIENT LEAD CABLE APPARATUS

BACKGROUND OF THE INVENTION

The present invention relates to an improved patient lead cable apparatus for electrocardiography.

To obtain information indicative of the electrical activity associated with the physiological functioning of the heart, electrodes are applied to the skin of a patient. In conventional twelve lead electrocardiography, ten electrodes are used. The electrodes are positioned on the patient's skin at locations established by a medical protocol. Four of the electrodes are placed on the patient to represent his/her limbs. These include the left arm electrode, the right arm electrode, the left leg electrode, and the right leg electrode. Six chest electrodes are placed on the patient's chest at various locations near the heart. The electrodes are connected to an electrocardiograph by patient lead cable apparatus.

The signals in the electrodes are combined in various combinations, termed "leads" to provide the desired electrocardiograph information to the electrocardiograph. An analog recording of the information produced on a strip chart recorder or cathode ray tube is used for diagnostic or other purposes. Or, the information may be digitized for analysis or display purposes.

Each of the ten electrodes requires a connecting wire in the patient lead cable apparatus leading to the electrocardiograph. In the past, the wires have often been separate and the ten connecting wires have inevitably become tangled when the apparatus is used. The need to at least partially untangle the wires when applying and connecting the electrodes on the patient's chest makes the application of the ten leads a time-consuming and tedious task. It further increases the possibility that errors will occur in placing the correct electrode at the proper location and in connection the correct electrode to the proper lead.

SUMMARY OF THE PRESENT INVENTION

It is, therefore, the object of the present invention to provide an improved electrocardiographic patient lead cable apparatus that lessens or avoids the tangling of the wires that has heretofore occurred, thereby facilitating connection of the wires to the electrodes and reducing the time required for such application. It is the further object of the present invention to provide a patient lead cable apparatus that aids in connecting the correct electrode to the proper lead. The present invention can also be used to aid in positioning the correct electrode at the proper location on the skin of the patient. It is yet another object of the present invention to provide patient lead cable apparatus having an improved lightweight, compact connector for connecting the electrodes to the electrocardiograph.

Briefly, the electrocardiographic patient lead cable apparatus of the present invention comprises an elongated cable part and a connector. The cable part has a plurality of connecting wires with couplers for the electrodes. The connecting wires are joined together for varying portions of their length to form a flat common portion of the cable part. The common portion is connected at one end to the connector. The connecting wires separate from the common portion at the selected locations along the extension of the common part from the end connected to the connector to form relatively short separated connector wires.

The lead cable apparatus so formed facilitates connection of the proper lead to the correct electrode when the electrodes are applied and positioned on the patient's chest in accordance with the medical protocol. Or, the electrode may be connected to the wires prior to application to the patient's chest. The lead cable apparatus, with the electrodes so connected, will then facilitate correct placement of the electrodes at the proper locations when the apparatus is laid on the chest of the patient. The commonly connected portion of the lead cable part, as well as the shortness of the connecting wires separated therefrom, reduces or eliminates tangling of the connecting wires.

The lightweight, compact connector is formed of a hard, dimensionally stable plastic surrounded by a flexible plastic covering. A flange member depends from a body of the connector for insertion in a mating receptacle in the electrocardiograph. The flange has a key means and a friction means for engaging the electrocardiograph receptacle. The body of the connector includes a resistor for each of the connecting wires to provide electrical protection to the electrocardiograph in the event of defibrillation. The end portion of the connector containing the depending flange may have a trapezoidal configuration which reduces the size of the connector.

BRIEF DESCRIPTION OF THE DRAWINGS

The present invention, including its construction, use, features, and advantages will be further understood from the following detailed description thereof taken in conjunction with the drawing. In the drawing:

FIG. 1 is a plan view of a patient lead cable according to the present invention;

FIG. 2 is a side view of the connector portion of the patient lead cable apparatus;

FIG. 3 is an end view of the patient lead cable connector portion;

FIG. 4 is a bottom view of the connector portion of the patient lead cable apparatus;

FIG. 5 is a cross-sectional view of the patient lead cable connector portion taken along the line 5—5 of FIG. 2; and FIG. 6 is a cross-sectional view of the patient lead cable connector portion taken along the line 6—6 of FIG. 3.

DETAILED DESCRIPTION

As shown in FIG. 1, electrocardiographic patient lead cable apparatus 10 comprises two main components: cable part 12 and connector 14.

Cable part 12 may comprise a plurality of individual connecting wires 12a through 12j. Each of the wires comprises a metallic central conductor, covered by an extruded plastic insulating sheath. As shown in FIGS. 1 and 2, the sheaths of adjacent connecting wires are joined together for varying portions of their lengths so that cable part 12 has a common, flat configuration, cable portion 16 comprised of a plurality of integrally connected adjacent connecting wires lying in a common plane. Other configurations or joinder techniques may be used, if desired.

Each of the connecting wires 12a through 12j terminates in an electrode connector 17. Connectors 17 are connected to the electrodes 18 applied to the patient, one such electrode being shown in FIG. 1 for illustrative purposes as connected to connector 17 of connecting wire 12c. Connector 17 may comprise a socket for releasably retaining a mating projection provided on electrode 18. Electrode 18 may be of either the disposable type or the reusable type. Disposable electrodes are typically formed to include a sheet of conductive film having a conductive adhesive thereon for retaining the electrode on the patient. Reusable electrodes typically comprise a metallic cup having a bulb which may be squeezed to draw a vacuum in the cup when the electrode is placed on the skin of the patient.

In accordance with the present invention and to facilitate connection of the proper lead to the correct electrode and the positioning of the correct electrode at the proper location on the body of the patient, connecting wires 12a through 12j are of differing lengths and branch off from the common cable portion 16 at different locations along the length of portion 16. Connection wires 12a and 12b branch off at the end of cable portion 16, i.e. at the left hand terminus of the cable portion when same is viewed as in FIG. 1. Connecting wire 12a is connected to the electrode positioned on the body to produce the right leg (RL) electrocardiographic signal and is so designated on FIG. 1. Connecting wire 12b is connected to the electrode placed on the body to obtain the electrode signal designated right arm (RA).

Connecting wire 12c branches off common flat cable portion 16 closer to connector 14 than connecting wires 12a and 12b. Connecting wire 12c is connected to the electrode 18 positioned on the body of the patient to produce the electrocardiographic signal designated left arm (LA).

Connecting wires 12d through 12i are branched off cable portion 16 at intervals along the medial part of cable portion 16. Connecting wires 12d through 12i are connected to the electrodes providing the chest signals to the electrocardiograph. These electrodes and connecting wires are commonly designated $V_1$ through $V_6$, as shown in FIG. 1. The electrodes are placed on the chest of the patient with the electrode $V_1$ connected to wire 12d being placed in the vicinity of the sternum, the electrode $V_6$ connected to the wire 12i being placed below the armpit of the patient, and the remaining electrodes $V_2$–$V_5$ connected to wires 12c through 12h being placed intermediate the $V_1$ and $V_6$ electrodes.

The last connecting wire to branch off common cable portion 16 is connecting wire 12j. This wire is connected to the electrode generating the left leg (LL) signal.

It will be appreciated that by branching connecting wires 12a–12j off cable portion 16 at various positions or intervals along its length, connection of the proper lead to the correct electrode is simplified, since when lead cable apparatus 10 is appropriately laid on the chest of the patient, each of the connection wires will lie at a location proximate to the corresponding electrode that has been applied at the proper location on the chest of the patient. The electrodes may then be simply and easily connected to the electrodes on the chest of the patient. A reduction or avoidance of tangling of the electrode leads is obtained by the presence of common cable portion 16 in which the connecting wires are joined together. It is further facilitated in that the length of the connecting wires 12a–12j not connected together in common cable portion 16 can be made short as possible commensurate with the proper positioning of the electrodes, thereby reducing the length of individual connecting wires subject to tangling.

Or, if desired, electrodes 18 may be connected to connecting wires 12a through 12j prior to application to the chest of the patient. When lead cable apparatus 10 is appropriately laid on the chest of the patient, the lead cable apparatus will also assist in placing the correct electrode at the proper location on the chest due to the branching of connecting wires 12a through 12j off common portion 16 and the lengths of the various connecting wires.

Electrocardiographic lead cable apparatus 10 also features an improved connector 14 for facilitating connection of the apparatus to the electrocardiograph. The connector is light in weight and small in physical size.

In exterior configuration, connector 14 has a body 22 and a flange 24. One end of body portion 22 comprises a generally flat, sheath like portion 26 for receiving common flat cable portion 16. Extending from portion 26, connector 22 includes a truncated pyramidal portion 28, a generally parallelepipedal portion 30 abutting pyramidal portion 28, and a terminal portion 32 that is trapezoidal in cross section, in both its orthogonal planes.

Such a configuration provides a connector 14 that can be easily gripped, yet is light weight and compact in physical dimensions, thereby facilitating its connection to the electrocardiograph.

As shown most clearly in FIG. 5, the exterior of body 22 may be covered with a flexible plastic covering 34, formed, for example, of polyvinyl chloride, that facilitates gripping the connector during connection and disconnection from the electrocardiograph. The internal component 35 of body 22 is formed of a hard plastic, such as polypropylene, that can be injection molded about the electrical elements of connector 14, as can be seen from FIG. 5 and can exhibit a high dimensional stability.

Flange 24 is formed of the hard plastic integrally with internal body component 35, the hard plastic being capable of withstanding the wear attendant the insertion and removal of flange portion 24 in a corresponding receptacle in the electrocardiograph. The dimensional stability of the hard plastic also facilitates the insertion and removal of the flange 24 in the receptacle in the electrocardiograph.

One of the side surfaces of flange 24 may contain a truncated triangular depression 36, as well as a curved cut out portion 38. Depression 36 and cut out portion 38 are keyed to mating components in the electrocardiograph to ensure connector 14 is connected to the electrocardiograph with the proper orientation. Ramp like portions 40 on the ends of flange 24 serve as friction elements to assist in retaining portion 24 in the mating receptacle of the electrocardiograph.

As shown in FIG. 6, the metal conductor of each connecting wire 12a through 12j is connected through a resistor 42 contained in the internal component 35 of connector 24 to a printed circuit board 44, also contained in internal component 35. In the event a defibrillator is used to apply a high-voltage electrical heart stimulation signal to the patient for resuscitation or other purposes, the resistors 42 in connector 14, serve to protect the electrocardiograph from the high voltages and high peak currents associated with defibrillation. As shown most clearly in FIG. 6, portions of the conductors of certain connecting wires and the associated resistors may be covered with an insulating coating 45 to ensure that short circuits among the conductors do not occur in connector 14.

Printed circuit board 44 is connected to socket member 46 located in flange 24 and having a socket 48 corresponding to each of the connecting wires. See FIG. 4. Sockets 48 engage corresponding male members when flange 24 is inserted in the mating receptacle in the electrocardiograph.

We claim:

1. Electrocardiographic patient, unitary lead cable apparatus for connecting a plurality of electrocardiographic electrodes to an electrocardiograph, the electrodes being applied at spaced locations on upper and lower portions of the body of a patient, said apparatus comprising:

an elongated cable part and a connector part;

said cable part having first and second ends between which said cable part extends, said cable part being joined at said first end to said connector part, said cable part comprising a plurality of connecting wires having connectors for the electrodes, said connecting wires being joined together for varying portions of their length along said cable part to form a common portion for said cable part extending from said first end toward said second end, said connecting wires separating from said common portion at selected points spaced along said common portion to form separated connecting wires, the separation of said connecting wires at said points facilitating connection to the electrodes at the spaced locations on the upper and lower portions of the body of a patient;

certain of said separated connecting wires for the electrodes being located at a medial portion between said first and second ends of said cable part for attachment to spaced locations in a common region on the upper portion of a body of a patient;

certain other of said separated connecting wires for the electrodes being located on opposite sides of the medial portion of said cable part for attachment to other spaced locations on the upper and lower portions of a body of a patient;

the lengths of said separated connecting wires being chosen to correspond to the distance between the common portion and the particular spaced location on the upper and lower portions of the body of the patient;

said connector part having means for connecting said lead cable apparatus to the electrocardiograph.

2. Electrocardiograph patient lead cable apparatus according to claim 1, wherein the length of the separated connecting wires is short compared to the length of said common portion from said first end.

3. Electrocardiographic patient lead cable apparatus according to claim 1, wherein said connecting wires are joined together to form a flat common portion for said cable part.

4. Electrocardiographic patient lead cable apparatus, according to claim 1 wherein certain of the electrodes comprise limb electrodes and wherein said connecting wires for the limb electrodes are separated from said common portion proximate to said second end of said cable part.

5. Electrocardiographic lead cable apparatus according to claim 4 wherein an electrode comprises a further limb electrode and wherein said connecting wire for the further limb electrode is separated from said common portion at a location spaced from said second end of said cable part.

6. Electrocardiographic lead cable apparatus according to claim 5 wherein an electrode comprises another limb electrode and wherein said connecting wire for the another limb electrode is separated from said common portion at a location spaced from said second end of said cable part, and at a location closer to said connector part than said connecting wire from said further electrode.

7. Electrocardiographic patient lead cable apparatus according to claim 6, wherein a plurality of the electrodes are applied at spaced locations on the chest of the patient to comprise chest electrodes and wherein said connecting wires for said chest electrodes are separated from said common portion at locations intermediate said first and second ends of said cable part and between the separation of the connection wire for the further limb electrode and the separation of the connection wire for the another limb electrode.

8. Electrocardiographic patient lead cable apparatus according to claim 5, wherein a plurality of the electrodes are applied at spaced locations on the chest of the patient to comprise chest electrodes and wherein said connecting wires for said chest electrodes are separated from said common portion at locations intermediate said first and second ends of said cable part.

9. Electrocardiographic patient lead cable apparatus according to claim 4, wherein a plurality of the electrodes are applied at spaced locations on the chest of the patient to comprise chest electrodes and wherein said connecting wires for the chest electrodes are separated from said common portion at locations intermediate said first and second ends of said cable part.

10. Electrocardiographic patient lead cable apparatus according to claim 1, wherein a plurality of the electrodes are applied at spaced locations on the chest of the patient to comprise chest electrodes and wherein said connecting wires for the chest electrodes are separated from said common portion at locations intermediate said first and second ends of said cable part.

11. Electrocardiographic patient lead cable apparatus according to claim 1 wherein said connector part comprises a body having a flange extending therefrom, said flange having connection means and being suitable for mating with a corresponding receptacle in the electrocardiograph, wherein said body has an internal component integrally formed with said flange, and wherein said flange and said internal component are formed of a plastic of high dimensional stability which is covered by a flexible plastic covering.

12. Electrocardiographic patient lead cable apparatus according to claim 11, wherein said body includes resistors intermediate said connecting wires and said connection means of said flange.

13. Electrocardiographic patient lead cable apparatus according to claim 11, wherein said flange contains keying means engageable with the receptacle of the electrocardiograph.

14. Electrocardiographic patient lead cable apparatus according to claim 11, wherein said flange includes friction means assisting in retaining said flange in the receptacle of the electrocardiograph.

15. Electrocardiographic patient lead cable apparatus according to claim 11, wherein said body has an end portion from which said flange at least partially extends, said end portion being formed with a trapezoidal configuration in a pair of orthogonal cross-sectional planes.

16. Electrocardiographic patient lead cable apparatus for connecting electrodes applied to a patient to an electrocardiograph, said apparatus comprising:

a lead cable part and a connector, said lead cable part having first and second ends between which said lead cable part extends, said lead cable part being joined at said first end to said connector, said lead cable part comprising a plurality of connecting wires having couplers for the electrodes, said connecting wires being joined together for varying portions of their length along said cable part to form a common portion for said cable part extending from said first end towards said second end, the length of the portion of said connecting wires not joined together being minimized compared to the length of said common portion in order to reduce the possibility of tangling said connecting wires, said connector comprising a body having a printed circuit board therein and a flange depending therefrom, said flange having connection means in the form of a socket member and being suitable for mating with a corresponding receptacle in the electrocardiograph, said body of said connector being covered with a flexible plastic covering, each of said connecting wires having a resistor for protecting the electrocardiograph from high voltages and high peak currents, each of said resistors being sealingly contained within said body and connected to said printed circuit board, said printed circuit board connected to said socket member in said flange, said socket member having a socket corresponding to each of said connecting wires.

17. Electrocardiographic patient lead cable apparatus according to claim 16, wherein said connector body has an internal component integrally formed with said flange and wherein said flange and said internal component are formed of a plastic of high dimensional stability which is covered by said flexible plastic covering.

18. Electrocardiograph patient lead cable apparatus according to claim 16, wherein said connection means contains a female connection adapted to mate with a male connection in the electrocardiograph.

19. Electrocardiographic patient lead cable apparatus according to claim 16, wherein said flange contains keying means engageable with the receptacle of the electrocardiograph.

20. Electrocardiographic patient lead cable apparatus according to claim 16, wherein said flange includes friction means assisting in retaining said flange in the receptacle of the electrocardiograph.

21. Electrocardiographic patient lead cable apparatus according to claim 16, wherein said body has an end portion from which said flange at least partially extends, said end portion being formed with a trapezoidal configuration in a pair of orthogonal cross-sectional planes.

* * * * *